Figure 1:
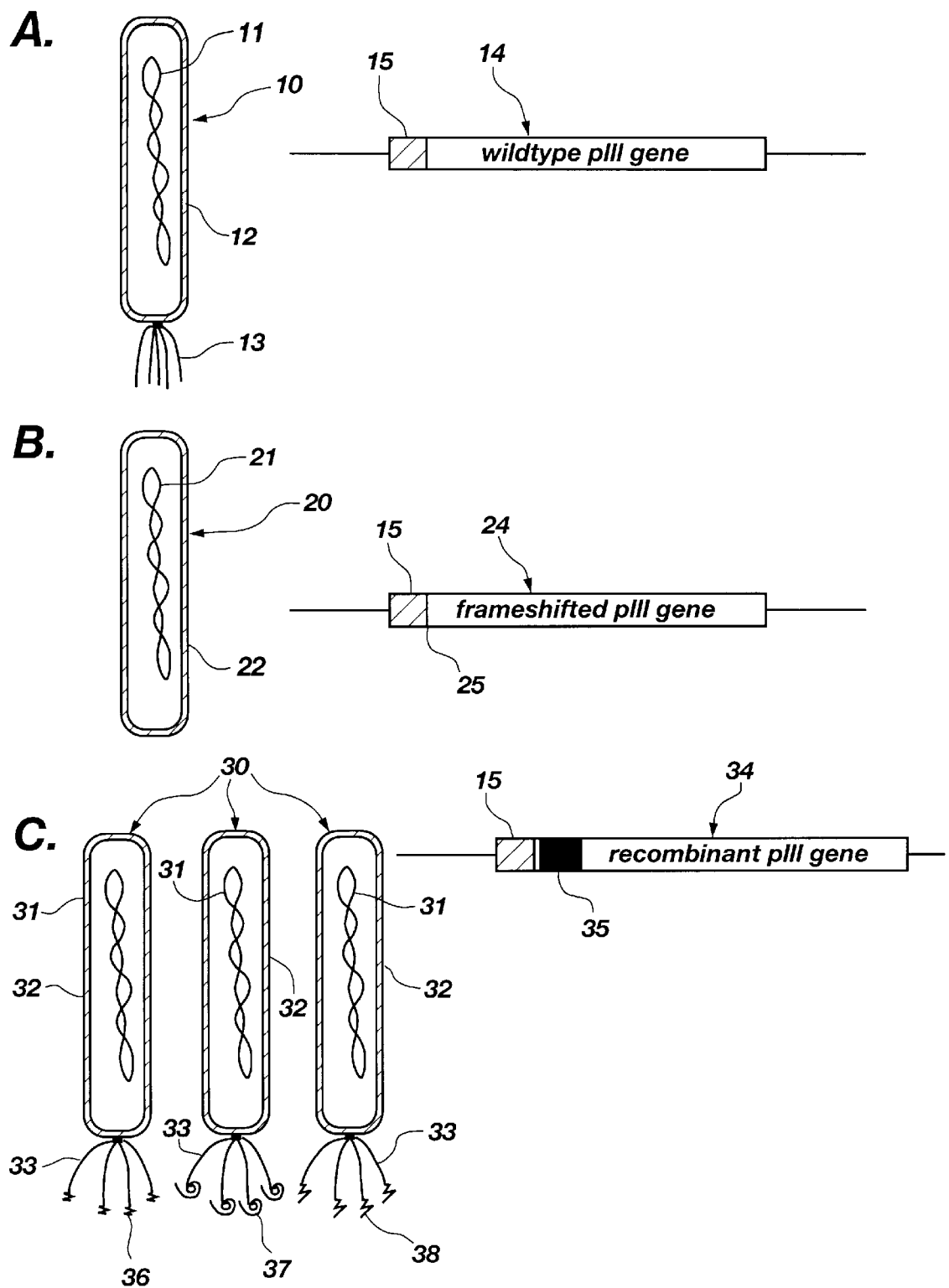

United States Patent [19]

Olivera et al.

[11] Patent Number: 5,885,780
[45] Date of Patent: Mar. 23, 1999

[54] METHOD OF OBTAINING SMALL CONFORMATIONALLY RIGID CONOPEPTIDES

[75] Inventors: Baldomero M. Olivera, Salt Lake City; David R. Hillyard, Holiday; Richard A. Myers, Salt Lake City, all of Utah; Jamie K. Scott; George P. Smith, both of Columbia, Mo.

[73] Assignees: University of Utah, Salt Lake City, Utah; The Curators of the University of Missouri, Columbia, Mo.

[21] Appl. No.: 733,095

[22] Filed: Jul. 19, 1991

[51] Int. Cl.⁶ .................................................. G01N 33/53
[52] U.S. Cl. ..................... 435/7.1; 435/69.1; 435/70.1; 435/71.1; 435/71.2; 435/252.3; 435/471; 436/63; 436/501
[58] Field of Search ............................ 530/317, 324–327, 530/855, 857; 435/6, 69.1, 70.1, 71.1, 71.2, 91, 113, 172.3, 252.3, 320.1, 240.2, 810; 436/63.501; 536/27; 935/6, 23, 79, 80

[56] References Cited

PUBLICATIONS

McIntosh et al. Arch. Biochem. Biophys, vol. 218, 1982, pp. 329–343.
Cruz et al, Biochemistry, vol. 28, 1989, pp. 3437–3442.
Rivier et al, J. Biol. Chem, vol. 262, 1987, pp. 1194–1198.
Olivera et al., Science, vol. 230, 1985, pp. 1338–1343.
Olivera et al. Science, vol. 249, 1990, pp. 257–263.
Devlin et al, Science, vol. 249, 1990, pp. 404–406.

*Primary Examiner*—Laurie Scheiner
*Attorney, Agent, or Firm*—Thorpe, North & Western, L.L.P.

[57] ABSTRACT

A method for separating, identifying and purifying small, conotoxin-like rigidly conformed peptides ("conopeptides") containing multiple Cys residues comprises forming a cono-effector library, each member of which has a nucleic acid encoding a potential conopeptide sequence. The conoeffectors are expressed such that they are exposed on the surface of a bacteriophage. These bacteriophage are screened for binding to a target protein molecule, and receptors in particular, to separate and bind phage having affinity for the target protein. Reiterative screening, if required, is used to enrich and yield a phage carrying the bound conopeptide of the desired specificity and affinity. The enriched phage are then subjected to DNA sequencing to determine the conopeptide sequence including the position of the Cys residues. The chemical structure information gathered, coupled with the binding specificities to the target protein, permits the genetic or synthetic preparation of a large variety of small rigidly conformed disulfide rich peptides as pharmaceutical, pesticidal or other bioactive candidates.

21 Claims, 3 Drawing Sheets

A.

fUSE 5 Cloning Site

```
          TCG GCC GAC GTG GCC TGG CC TCT GGG GCC GAA  ACT
          AGC CGG CTG CAC CGG ACC GG AGA CCC CGG CTT  TGA
                           sfII released stuffer fragment
```

B.

fUSE 5/α   conotoxin-MI

```
TCGGCCGACGGGAGGTGCTGTCATCCCGCGTGCGGTAAAAACTATTCGTGCGGCGGCATTGAAGGTCGCGCTG GACCCCGGCTTTGA
AGCCGGCTGCCCTCCACGACAGTAGGGCGCACG                                        
                 patch sequence          fill in with DNA polymerase and ligate
                                                      with DNA ligase
 signal sequence

A.

fUSE 11 Cloning Site

```
                    BsaI                                BanII
                     ↓                                   ↓
        AT TCT CA|C AGC GGA GAC CTG GA GCC|CCT GGC GCT GAA ACT
        TA AGA GT|G TCG|CCT CTG GAC CT|CGG GGA CCG CGA CTT TGA
```

B.

fUSE 11/α   Conopeptide fusion library

DNA Construction

```
ATTCTCA|CAGCGGGAGGTGCTGTNNKNNKNNKNNKNNKTGCNNKNNKNNKNNKTGCGGCGGCATTGAAGGTCGTGGAGCC|CCTGGCGCTGAAACT
TAAGAGT|GTCG|                                                                |TCGGGGACCGCGACTTTGA
              → fill in with DNA polymerase and ligate with DNA ligase
```

Translation Product signal sequence | Gly Arg Cys Cys Xaa Xaa Xaa Cys....
....Xaa Xaa Xaa Xaa Cys Xaa Xaa Xaa Xaa Cys Gly Gly Ile Glu Gly Arg Gly Ala | gene 3 protein

C.

fUSE 11/α   Conopeptide fusion library

DNA Construction

```
ATTCTCA|CAGCTGT(NNK)6TGC(NNK)6TGCTGT(NNK)3TGT(NNK)4TGTGGCGGCATTGAAGGTCGTGGAGCC|CCTGGCGCTGAAACT
TAAGAGT|GTCG|                                                                |TCGGGGACCGCGACTTTGA
              → fill in with DNA polymerase and ligate with DNA ligase
```

Translation Product signal sequence | Cys Xaa Xaa Xaa Xaa Xaa Xaa Cys Xaa Xaa Xaa Xaa Xaa Xaa Cys Cys....
....Xaa Xaa Xaa Cys Xaa Xaa Xaa Xaa Cys Gly Gly Ile Glu Gly Arg Gly Ala | gene 3 protein

*Fig. 3*

METHOD OF OBTAINING SMALL CONFORMATIONALLY RIGID CONOPEPTIDES

This invention was made with government support under Contract No. N00014-88-K-0178 awarded by the Department of the Navy and under Contract No. GM-22737 awarded by the Department of Health and Human Services. The government has certain rights in the invention.

BACKGROUND OF THE INVENTION

This application relates to a method of generating, screening and identifying small disulfide rich conopeptides having high affinity and specificity for selected target proteins using cloning, and particularly, fusion phage technology.

The marine gastropod mollusks belonging to the superfamily Conacea, (also called Toxoglossa) are distinguished by the general presence of a toxin gland and a hollow tooth for delivery. This superfamily, comprising approximately 4000 species, perhaps 10% of all molluscan species diversity, is one of the most successful of all marine taxa. There are three main groups or families, i.e. the cone (Conus), the tower shells (Terebra) and the slit shells (Turris). All species are predators, the vast majority using venom as the primary means for subduing prey.

One factor that contributes to the success of this group is the remarkable biochemistry of their venoms. Conacea venom may be particularly important to understand in all of its facets. The biologically active components of at least some of these venoms are an unprecedented diversity of small, conformationally rigid peptides having specifically located Cys residues and multiple disulfide bonds. These peptides are amenable to known methods for chemical synthesis and structure determination. In addition, they are directly translated from genes, and can therefore be manipulated by state of the art molecular biological technologies.

Most information developed thus far, including biochemical analysis of venoms, have been done on species of the Conus family. However, a direct biochemical analysis of the venoms from the various species of the Terebra and Turnis families has not yet been carried out. The roughly 500 species of the Conus family can be divided into three groups on the basis of the prey they feed on, i.e. the worm-hunting, mollusc-hunting and fish-hunting species. Venoms of at least one species of each of these groups has been analyzed and the major biologically active components have been identified as small peptides, typically of about 10 to 30 amino acids in length. A particular Conus venom may have well over 50 different small peptides, many of them with different pharmacological specificity. From the numerous peptides which have been purified from various Conus species, a number of generalizations have emerged which form the basis for the presently claimed invention. The peptides isolated from venom of all the various species within the Conacea superfamily are generically referred to in this description as "conotoxins".

Each conotoxin peptide appears to be specifically targeted to a macromolecular receptor, interfering with its normal function. The conotoxins can have very high affinities for their receptors. In the case of certain ω-conotoxins, for example, subpicomolar affinities are achieved for their high-affinity Ca++ channel targets. A key feature that contributes to the high affinity and specificity of the conotoxin peptides is attributed to their fixed, relatively rigid conformation. Normally, peptides in the 10 to 30 amino acid range would not have a specific fixed conformation because of their small size. Under most physiological conditions, it takes a polypeptide of about 40–50 amino acid residues before the sum total of non-covalent forces, (hydrogen bonds, hydrophobic interactions, and the like) is sufficient for a specific conformation to be stable. The vast majority of the conotoxin peptides are conformationally restrained by covalent cross-linking through multiple disulfide bonding. Typically between about 20 to 50% of all amino acids in a conotoxin peptide are Cys residues. Conotoxin peptides have some of the highest known densities of disulfide bonding in any biological system. Peptides from Conus venoms have been isolated that are only 12 amino acids long with three disulfide bonds. In general, only one disulfide bonded configuration of a particular toxin exhibits high affinity for the specific receptor target. Although some conotoxins have only two disulfide bonds (notably the α-conotoxins which target to nicotinic acetylcholine receptors), more commonly the major paralytic conotoxins found in Conus venom have three disulfide bonds (in the fish-hunting cones, the μ-conotoxins which target to muscle voltage-sensitive Na channels and the ω-conotoxins which target to presynaptic voltage sensitive Ca channels). For the latter, there are 16 possible disulfide bonded configurations. Folding smaller peptides into one specific configuration is a biochemical problem which the cone snails had to solve before they could efficiently use such small peptides as high affinity ligands for paralysing their prey.

Small, conformationally constrained peptides are ideal for a wide variety of biotechnology applications. Their small size facilitates access to specific target receptors. Specific cross-linking of disulfide bonds allows these small peptides to assume a relatively rigid structure that increases the probability of high affinity interaction with target molecules. Still, the variation of peptide structure afforded by variation in amino acid sequence in such peptides is enormous. Natural variants among peptides following this architectural design have been found to target a great diversity of target types.

One feature that has emerged from sequencing many conotoxin peptides is that most of them fall into characteristic patterns of disulfide forming Cys residue arrangements. The major, or standard framework, patterns are represented by the following formulas with Cys being represented by "C" and "--" representing a variable grouping of other amino acids:

| | | |
|---|---|---|
| "2-loop" framework | CC--C--C | (Formula I) [Seq. ID NO: 15] |
| "3-loop" framework | CC--C--C--CC | (Formula II) [Seq. ID NO: 16] |
| "4-loop" framework | C--C--CC--C--C | (Formula III) [Seq. ID NO: 17] |

These characteristic Cys arrangements are found as a dominant structural feature in conotoxin peptides from all three feeding classes of the Conus family and may be present in the venoms of all families within the Conacea superfamily. The conotoxin peptide sequence information from mollusk-hunting venoms is typical. Of 17 peptides sequenced sufficiently for assessing the Cys residue arrangement, two peptides had the standard 2-loop configuration (Formula I), five had the standard 3-loop structure (Formula II) and nine had the standard 4-loop framework (Formula III). One peptide did not fit a standard framework and had a minor 5-loop configuration. The actual disulfide bonding in at least one member of each of the standard frameworks has been determined. The disulfide bonds were formed between the first and third and second and fourth Cys residues in the 2-loop structure and between the first and fourth, second and fifth and third and sixth residues respectively in the 3-loop and 4-loop frameworks.

It is hypothesized that the standard loop structures are established in the conotoxins because the Conus snails have evolved genetic mechanisms for efficiently and rapidly generating variant sequences, mechanisms specifically geared to using the standard Cys frameworks. In this way, the Conus snails are able to achieve a remarkable sequence plasticity in their peptides and a corresponding pharmacological diversity even though the same Cys frameworks, and hence, disulfide bond configurations, are used again and again. For example, the major group of conotoxins which target to Na channels have a standard 3-loop framework but another conotoxin targeting to the same Na channel has the standard 4-loop framework. The two peptides have no apparent homology and appear to have evolved independently. In addition, 4-loop Ca channel targeted peptides, with no affinity for Na channels and no homology to the 4-loop Na channel peptide are present in the same venom. A single venom from a Conus snail comprises numerous small peptides, most of which exhibit standard 2-, 3- and 4-loop Cys frameworks. Despite the small numbers of different Cys frameworks, the diversity of peptides in any given Conus venom is truly remarkable. Moreover, each of the thousands of species of the Conacea superfamily may have its own distinctive complement of peptide sequences. In the data obtained from ten species of the Conus family, no single peptide sequence has been found to occur in more than one venom. Therefore, it is believed that there are many thousands of peptides in the Conacea venoms each having its own distinctive pharmacological properties. As illustrative, one may consider the α-conotoxins which are the major post-synaptic paralytic toxins targeting to acetylcholine receptors. It has been found that each fish-hunting species has its own set of α-conotoxins, having sequences different from any other species.

The pharmacological complexity of a single venom may be illustrated by examining the in vivo effects of injecting each peptide from one size fraction of a single *Conus geographus* venom. This experiment is described in detail in Olivera et al., (1990) *Science* 249, pp. 217–232. The venom was eluted into fractions on a Sephadex G-25 column. One major fraction was further separated by HPLC using a VYDAC C18 column and a trifluoroacetic acid-acetonitrile gradient. The elution profile showed numerous peaks when absorbance at 210 nm is plotted as a function of elution time. Each peak, consisting of either a single peptide or mixture of several peptides, was tested for biological activity by injecting from 0.5 to 2 nmol intracranially into mice and the CNS response elicited was recorded. In many cases the activity observed is either the symptomatology induced by the most potent component or a composite of symptoms from several peptides. Whether the activity is the result of a single conotoxin or mixture of conotoxins the following responses were observed, each coming from a single peak in this one size fraction, (1) head swinging, (2) circular motion, (3) dragging back legs, (4) sleeper/climbing, (5) uncoordinated, (6) twisted jumping, (7) paralysis, (8) kicking on back and scratching, (9) depressed activity, (10) comatose (lethal to at least one animal), (11) paralysis (lethal to at least one animal), (12) depressed activity, (13) trembling, (14) dragging (lethal to at least one animal), (15) depressed followed by hyperactivity (lethal to at least one animal), (16) normal, (17) scratching and convulsion (lethal to at least one animal), (18) convulsion and bleeding (lethal to at least one animal), (19) convulsion (lethal to at least one animal) and (20) normal.

It is apparent from the above that the conotoxins have distinctive properties which make them of particular interest for biotechnological applications. Although there is a remarkable pharmacologic diversity of conotoxins, each peptide is specifically targeted. In certain cases, the conotoxins are able to discriminate between closely related subtypes of a receptor target.

One reason for some of the unique properties of the conotoxins may well be a response to the relentless selection for rapid paralysis. The unusually small size of the conotoxin peptides may have evolved to facilitate the efficient dissemination of the toxins through the body of the prey. A small peptide of 10–30 amino acids will cross permeability barriers (such as the blood vessels of fish) much more quickly than a typical 50–90 amino acid proteinaceous toxin of snakes or scorpions. In this respect, the conotoxins can literally immobilize the prey 1–2 seconds after injection of the venom and effect complete paralysis a few seconds later.

Molecules of this type have an expanding usefulness as agents capable of targeting a vast variety of receptors and ion channels on the surface of many different cell types. These molecules will be useful in the design and testing of drugs targeting a variety of therapeutically important receptors, and in the design of agriculturally important agents such as pesticides. These peptides are unique ligands which potentially affect the function of their target proteins.

The major object of this invention is the de novo, snail-free generation of conotoxin-like peptides. Although the natural complement of conotoxins has many potential applications, the ability to produce novel peptides in vitro with predetermined target specificity would vastly expand this potential. It has been shown by Olivera et al., (1990) *Science*, 249, pp 217–232, which is incorporated herein by reference, that this general class of rigid, mulitple disulfide-linked peptides can be ligands of exquisitely refined specificity. At this time, no conotoxin-like peptide has yet been generated in vitro with a novel specificity. The invention described is drawn to a means of producing ligands with the same general characteristics as the natural conotoxins, i.e., peptides with high affinity and specificity for a target receptor, which can be chemically synthesized, and that have a relatively rigid conformation due to multiple disulfide bonds. When such peptides are bound to their receptor target, they affect the biological activity of that target. Such conotoxin-like peptides will, in this description, be called either "conoeffector peptides" or "conopeptides", terms which will be used interchangeably. Conoeffector peptides with particular biological activity will be identified by screening a general conopeptide library for clones which bind to a particular receptor protein and affect its biological activity. The conoeffector peptides so identified will yield sufficient chemical-structure information to allow peptidomimetic drug design. In addition, further rounds of screening could yield conopeptides with still more refined receptor or phylogenetic specificities.

Although the natural spectrum of peptides provided by the conotoxins is highly diverse, specific application will require peptides with receptor or phylogenetic specificities which may not be found directly in the set of natural conotoxin peptides. For example, in the field of pesticides, it may be desirable to have toxins that specifically kill only one order or insects, but do not affect other arthropods, nor animals in other phyla. Such specificity is unlikely to be found in the set of natural conotoxins because they are targeted in vivo either to vertebrates, mollusks, or three phyla of worms, and not to insect receptors. However, in principle, it should become possible to carry out phylogenetic focusing in vitro. Once a peptide structure has been found which targets to a particular target protein or receptor type, it should be possible to use molecular genetics to select variants with the desired phylogenetic specificity. Thus, in the case of insecticides, the lead structure might be a "broadly focused" or even a phylogenotically non-discriminating conotoxin structure which acts on the target insect. A library could then be constructed, each containing a variant of the lead conotoxin sequence. Variants can be selected to bind the target insect receptor, but show no binding to homologous receptors in other taxa.

The same reasoning will also apply to the design of conopeptides having other biological and/or pharmacological applications.

Several potential applications of in vitro-generated cono-effector peptides are based on the potential ability of the conopeptides to distinguish between closely related subtypes of a particular receptor target. A major problem in drug design, for example, is to rationally minimize side effects. In recent years, recombinant DNA technology has revealed that multiple subtypes exist for practically every cell-surface receptor involved in intercullular signaling and signal transduction. Although a drug may be targeted to a particular therapeutically relevant receptor target, it may interact with closely related subtypes as well. The latter interactions are the probable cause of the side effects of many drugs. Conceptually, the most straightforward way to circumvent this problem is to develop agents that only interact with therapeutically relevant receptor subtype targets with no cross reactivity to related receptor subtypes.

Conotoxin structures clearly have the potential for such refined pharmacological targeting. It has been demonstrated that certain conotoxins can exhibit remarkable receptor subtype discrimination. In particular, the ω-conotoxins, which target to calcium channels, show a tissue specificity with regard to calcium channels that is exhibited by no other ligand that has been designed by the pharmaceutical industry so far. Thus, the dihydropyridine drugs will affect calcium channels not only in skeletal muscle, cardiac muscle and smooth muscle but in neuronal tissue as well. In contrast, the ω-conotoxins target to certain neuronal calcium channel subtypes and show a $>10^8$ fold discrimination index against calcium channels which are non-neuronal in the most favorable cases. This remarkable ability to discriminate between what are probably closely related receptors demonstrates that the basic conotoxin structural motifs are capable not only of having very high affinity for a particular receptor subtype, but a high discrimination index against closely related subtypes.

In principle, conoeffector peptides can be generated in vitro which affect the activity of the desired subtype of a particular receptor, but are screened not to bind other closely related subtypes at all. Therefore, this invention has the potential to provide the pharmaceutical industry with a rational methodology for designing drugs with minimal undesirable side effects. In principle, it should be possible to design an ω-conotoxin-like molecule that only is targeted to a single calcium channel subtype with no cross reaction against any other calcium channel, nor other receptors. This has great potential application, since calcium channels control many specific properties of nerve cells, including neurotransmitter release. Other specific applications include drugs for Parkinson's disease, schizophrenia and depression. The side effects of many therapeutically effective drugs for these conditions is a continuing problem. Some of the most effective drugs affect the metabolism of the neurotransmitters dopamine and serotonin. The biological effects of these neurotransmitters have been shown to be mediated through dopamine receptors and serotonin receptors, both of which are present as multiple subtypes, encoded by multiple genes. Many of these receptor subtypes have recently been cloned, and can thus be used to screen conopeptide libraries. The possibility of obtaining a small rigid peptide specifically targeted for agonist or antogonist activity to each dopamine receptor subtype would have obvious implications in drug development for Parkinsonism and schizophrenia.

The basis for using an in vitro approach for the focusing of conopeptides to specific protein targets requires a system into which conopeptide modules can be cloned. The sequence of the conopeptide module can be varied by inserting oligonucleotides with random nucleotide sequences in selected positions. The variant conopeptide sequences could then be screened for binding to receptors or other selected targets. Preferably the conopeptides will be cloned such that they are displayed on the surface of a carrier protein or in a cell compartment where they can be exposed and, if active, bound to a specified receptor or other target protein molecules.

A system wherein other peptides have been successfully cloned and screened for binding specificity has recently been described by two of the inventors herein and is referred to as "fusion phage", e.g. see Scott et al., Searching for Peptide Ligands with an Epitope Library, *Science,* 249, 386–390 (Jul. 20, 1990) which is incorporated herein by reference. "Fusion phage" are filamentous bacteriophage vectors in which foreign sequences are cloned into phage gene III and displayed as part of the gene III protein (pIII) at one tip of the virion.

In the fusion phage techniques of Smith et al., supra, a library was constructed of phage containing a variable cassette of six amino acids. The variable hexapeptide modules, when fused to the bacteriophage, provides a library for the screening methodology that can examine $>10^{12}$ phages (or about $10^8$–$10^{10}$ different clones) at one time, each with a test sequence on the virion surface. The library obtained was used to screen monoclonal antibodies specific for particular hexapeptide sequences. The fusion phage system has also been used by other groups and libraries containing longer peptide inserts have been constructed as shown by Devlin et. al., (1990) *Science* 249, 404–406 and libraries displaying antibody variable domains are shown by McCafferty et.al., (1990) Nature 348, 552–554. The peptides, such as referred to by Smith et al. and Devlin et al., supra, have a disadvantage in the bacteriophage screening technique since they do not have rigid structure and usually have longer, flexible amino acid chains. In such long chain flexible peptides, potential interactive sites may tend to be masked by the folding of the peptide chain, thereby making it almost impossible to screen the library effectively. In addition, because the peptide inserts suggested by these articles are relatively flexible, the binding conformation may be assumed as only one of many alternative and thus the peptide module may not bind to a receptor site with as great affinity as is desirable. Indeed, the hexapeptide library of Scott et al., supra, has not produced binding clones for five different receptors used [Scott, (1991) *Trends in Biochemistry*, (in press)].

However, the conopeptide type molecules should be well suited for this type of screening since they have multiple disulfide bonds which give them a rigid structure that binds readily with the reactive sites of the receptors or other target protein molecules. Hundreds of millions of different conopeptides could be easily surveyed for tight binding to a receptor or other binding protein using a cloned library of conopeptides.

It would therefor be desirable to combine the structural information gleaned from the conotoxins with fusion phage technology in the design of such "conoeffector peptide" libraries. Such libraries would provide necessary information for identifying clones of phage bearing conopeptides which bind specifically, and with high affinity to a particular receptor and other target proteins, and affect their function. Once a clone has been isolated and identified as binding tightly to receptor, the encoded conoeffector peptide can be synthesized. Such receptor-targeted conopeptides could be used to obtain sufficient chemical-structural information to allow the design of any variety of pharmaceuticals, pesticides, or other bioactive agents limited only by the availability of appropriate receptor or other target protein molecules.

OBJECTS AND BRIEF SUMMARY OF THE INVENTION

The major object of this invention is the de novo, snail-free generation of conotoxin-like peptides.

Another object of the invention is to provide a method for the synthesis, identification and isolation of cloned conotoxin-like peptides (conopeptides) having binding specificities for receptors or other target proteins and affecting the biological activity thereof.

It is also an object of the invention to provide libraries of bacteriophage (or other vectors) carrying conopeptide modules on a surface protein (or within a cell) which are useful to screen for small rigid Cys-rich (where Cys stands for both cysteine and cystine) conopeptide ligands with novel specificities using target receptors or other protein molecules.

A still further object of the present invention is to provide a system for inserting conopeptide modules on a surface protein and being able to clonally screen, identify and chemically synthesize conoeffector peptides with affinity for a particular target receptor.

These and other objects may be accomplished by a system in which a cloned disulfide-rich small conoeffector peptide module, having amino acid sequences encoded by nucleic acids, each module with fixed disulfide positions but with the remaining amino acids being variable, referred to as a "conoeffector peptide library", is fused to a protein on the surface of a cell or virus (or in an intracellular compartment). Such libraries comprise hundreds of millions of clones, each of which displays a different conopeptide on the cell or viral protein (or in an intracellular compartment). As referred to above, such conoeffector modules are based on the general structure of the naturally occurring conotoxins, particularly in the presence of invariant multiple Cys residues involved in intramolecular disulfide cross-links, but which have intervening regions of variable amino acid sequences, which comprise loops on the conopeptide module by bridging of the invariant Cys residues.

Receptor or other target protein molecules are then used to screen the library for tight binding conoeffector conopeptides. If required, reiterative screening is carried out to yield conopeptides of the desired specificity and affinity. The set of peptides which bind the target receptor may be screened for failure to bind other closely related receptor subtypes. The structure of the conoeffector peptides are determined by DNA sequencing of the identified clones. The chemical structure information gathered, coupled with the binding specificities, permits the in vitro genetic or chemical synthetic preparation of a large variety of conopeptides as pharmaceutical, pesticidal, or other bioactive peptide candidates.

The conoeffector peptide libraries can be prepared using any suitable system wherein the conopeptide module is expressed on the surface of a living cell or virus or, in the alternative, in an intracellular compartment, and its sequence is encoded by nucleic acids. The system must be amenable to producing a large number, i.e. $\geqq 10^9$, clones. Preferably, the cloned conoeffector library will be prepared by insertion of the appropriate nucleotide sequences into a fusion phage vector for expression and display on the surface of bacteriophage. In the screening process conopeptide bearing phage are directly screened against target receptor or other protein molecules, the binding phage are enriched and the encoded conopeptide module, specifically identified by DNA sequencing. However, the invention is not limited to any particular method of library preparation. In its broadest aspects the oligonucleotides encoding a conopeptide or conotoxin-like peptide are inserted into a vector to provide recombinant DNA for transfecting a living cell where the recombinant DNA is amplified in an infectious form, suitably as bacteriophage, to provide the conotoxin-like peptide library consisting of conotoxin-like peptide modules. The library of phage bearing conotoxin-like peptide modules formed by amplification of the recombinant DNA in the living cell is reacted with the target protein to find and/or determine which conopeptide modules bind to the target.

The conopeptides which bind with specificity to target receptors (and particularly to novel or newly discovered receptors) and affect their biological activity, present a means for obtaining bioactive peptides quickly, relatively inexpensively and with precision which has heretofore been unknown in the synthesis and screening of small peptides. In addition, this technology yields rigid disulfide-rich peptides with novel receptor-target specificity, the conformation of which can be analyzed. Such peptides have never been generated de novo by a recombinant DNA based technology, or any other in vitro method.

DESCRIPTION OF THE DRAWINGS

FIGS. 1A., 1B. and 1C. illustrate diagrammatic representations of filamentous phage with the circular single-stranded DNA molecule inside the cylindrical coat and pIII protein represented at the bottom of the infectious phage particles and also showing a schematic representation of the pIII coat protein gene showing a fUSE vector, the cloning site and the nucleotide insert into the vector coded with conotoxin-like sequences.

FIGS. 2A., 2B. and 2C. illustrate the cloning site in a fUSE5 vector and illustrate both the oligonucleotide and amino acid sequences of a conotoxin construct and an α-conopeptide library for use with the fUSE5 vector.

FIGS. 3A., 3B. and 3C. illustrate the cloning site of a fUSE11 vector and illustrate both the oligonucleotide and amino acid sequences of an α and an ω conopeptide fusion library.

DETAILED DESCRIPTION OF THE INVENTION

The conopeptide molecules, as described above, are relatively short and have a relatively rigid structure imposed by the disulfide bonds. By determining the relative positions of the Cys residues in the peptide chain, a large variety of DNA sequences can be constructed wherein the DNA nucleotides encoding the Cys amino acid residues are positioned to be characteristic of the conotoxins while the remainder of the DNA can be varied, thus producing variable regions of DNA sequences encoding a vast number of peptides, wherein the position of the fixed Cys residues is conotoxin-like with the remaining amino acid residues being varied. It is possible that, among the amino acids which are varied, there will also be Cys residues, some or all of which can also participate in disulfide bond formation. Therefore, the conotoxin-like peptides may or may not have the exact frameworks as the natural conotoxins but will be sufficiently similar that the term "characteristic of conotoxins" or "conotoxin-like" is appropriate to define the general rigid structure of the conopeptides formed according to this invention. The small rigid conopeptides, when fused to the bacteriophage (bacterial virus) coat protein, potentially display ligands of higher affinity and exquisite selectivity to target receptors or other protein molecules. This provides a screening methodology that can examine $10^9$–$10^{10}$ phage clones at one time, each bearing a single conopeptide test sequence on the virion surface.

Conoeffector Module Preparation

The invention described herein takes advantage of the known structural properties of the natural conotoxin peptides in the design of novel peptides. These de novo generated conoeffector peptides similarly have multiple fixed Cys residues and disulfide bonds, and the initial design of "conoeffector" libraries will use the natural conotoxin Cys residue configuration. The conopeptide libraries comprise hundreds of millions of bacteriophage clones, each of which displays a different conopeptide module on its surface. These conopeptides are rigidly constructed 2-, 3-, or 4-loop (or even higher) Cys framework determinants on a phage coat protein that are similar in structure to the conotoxins in the locations of cystine residues, but which have regions of variable amino acid sequences. Therefore, each member of the conopeptide library will have a different nucleotide sequence encoding a conopeptide structure that is displayed by a bacteriophage.

In the construction of conopeptide modules it is preferable, if not essential, that the disulfide bonding of the Cys residues are specific to form the proper configuration. A method of producing such Cys-rich mature peptides utilizing prepropeptide molecules having a general architectural theme which probably directs the folding of the mature peptides into their proper bioactive configuration is disclosed in copending patent application Ser. No. 07/689,692 filed Apr. 18, 1991, Hillyard et al., Segregated Folding Determinants for Small Disulfide-Rich Peptides and is incorporated herein by reference. By using this technology conoeffector modules of 2-, 3-, 4- (and even greater) looped small mature peptides can be prepared wherein the amino acids besides the fixed Cys residues are varied. This variation can be accomplished with chemically synthesized oligonucleotides such that all positions in the mature peptide regions, except for codons encoding Cys residues, are varied to generate all possible amino acids in selected positions.

While this invention encompasses the use of conoeffector peptide modules in the preparation of conopeptide libraries, the particular manner in which these Cys rich peptides are constructed is not limited to the methods disclosed in the above referenced Hillyard et al. pending application. That application discloses one method of such preparation and attention is directed to that disclosure. However, conopeptides prepared or made available from any other means can also be screened for activity and binding to target receptors or other proteins.

Other Cys arrangements, such as C--C--C--CC--C [Seq.ID NO:18] and C--C--C--C--CC [Seq.ID No:19], which are used in other biological situations such as in the mammalian defensin family, and appear to have diverse pharmacological roles are also believed to be suitable to be classified as "characteristic of contoxins" or "conotoxin-like" in structure although not strictly conotoxin structure specific. It is believed that these frameworks, as well as others having multiple fixed Cys residues and specific disulfide bonding arrangements, will also function in the presently claimed invention and will therefore be broadly classified herein as conopeptide structures.

The only limitation in what is or is not a suitable conopeptide is that the location of the fixed Cys residues and disulfide bonding (i.e. framework and configuration) must be such that there is sufficient affinity or binding to the target receptor or other protein molecule to display biological activity. The disulfide structure of select conopeptides can be determined by chemically synthesizing the peptides, folding in vitro, separating the different conformers by HPLC and testing each for binding to target receptor and/or bioactivity.

Conopeptide Phage Libraries

In the construction of the conoeffector peptide library, each member of which has nucleic acids encoding a potential conopeptide sequence, the conoeffector modules are expressed such that they are either exposed on the surface of a cell or virus (or in an intracellular compartment). When the conoeffector modules are expressed in an intracellular compartment, the target receptor or protein molecule will also be contained within the cell where binding takes place instead of on the cell surface. Therefore, even though the invention is described primarily by the expression of conoeffector modules on a viral surface using bacteriophage technology, expression intracellularly is also considered to be included within the scope of the invention. As stated above, the invention is broadly drawn to any method wherein recombinant DNA encoding the conopeptide-like sequences are amplified in a living cell in infectious form to form the conopeptide-like library.

In a preferred embodiment, the conopeptide modules are expressed fused to a coat protein of a filamentous bacteriophage, so that the conoeffectors will be displayed on the surface of the virion and are potentially available to interact with an exogenous receptor target molecule. One suitable bacteriophage system, developed by one of the inventors herein, is disclosed in more detail in Smith, *Science,* 228, 1315–1317 (1985). Bacteriophage systems using fUSE phage as a vector in which the conopeptide module is expressed fused to the pIII coat protein are referred to as "fUSE/conopeptide phage". Besides its role as a vehicle for displaying conopeptide modules, the pIII coat protein is also required for infectivity of the virion. The construction of the phage fUSE5 vector used in the formation of conopeptide phage libraries is described in detail in Scott et al., *Science,* 249, 386–390 (1990).

The fUSE vector of Scott et al permits the genetic modification of the N-terminal domain of the phage pIII coat protein. Following the insertion of oligonucleotide sequences into a modified pIII gene reading frame on fUSE5 double-stranded RF DNA, variants of the pIII protein containing novel N-terminal sequences can be expressed on the surface of the phage. The design of oligonucleotide sequences encoding the conopeptide (conotoxin-like) sequences for insertion into the fUSE5 vector can result in the generation of libraries of conotoxin-like fusion proteins having conoeffector domains accessible for binding to target protein molecules such as receptors.

The α-conotoxins, by virtue of their small size, relatively simple disulfide crosslinking geometry, and well characterized receptor targets, afford a model system for the generation of conopeptide sequences by genetic engineering. The generation of libraries of α-conopeptide fusion peptides with fixed Cys residues of the α-conotoxins but containing variable intercysteine sequences may permit the generation and identification of conopeptides with specific affinities for broad and diverse classes of receptor or other protein molecules unrelated to the acetylcholine receptor. Another application is the identification of peptide sequences closely related to the natural family of α-conotoxins but having altered phylogenic or subtype specificity for nicotinyl acetylcholine receptors.

The preparation of a conotoxin-like library is schematically illustrated in FIG. 1. FIG. 1A. shows a normal filamentous phage 10 having the circular single-stranded DNA molecule 11 inside the cylindrical coat 12 and the pIII protein represented by the fibers 13 at one end of the phage particle. At the right is a schematic representation of the wild type pIII gene 14 showing the signal sequence 15. This N-terminal signal sequence of the pIII protein is necessary for its insertion into the outer membrane of the bacterial cell. The pIII protein is cleaved at the signal sequence site releasing the N-terminal signal sequence and mature pIII protein. When the phage 10 infects to a bacterium and the viral DNA enters the cell, it replicates, phage are produced and secreted, with each virion containing the same DNA sequence.

FIG. 1B. shows a non-infective fUSE vector phage 20 containing a single-stranded DNA molecule 21 inside the cylindrical coat 22 but containing no pIII protein. The pIII gene 24 has been modified by a frameshift mutation so that the pIII protein is not produced. In the absence of a frame restoring insert, the phage particles lack the pIII protein and, consequently, the phage is non-infective. The fusion cloning site 25 for an insert is shown in FIG. 2B, and is located at or near the region encoding the N-terminus of the mature pIII coat protein.

FIG. 1C. shows phage particles 30, each with a different single-stranded DNA moleculeand inside the cylindrical coat 32and each with a different recombinant pIII protein 33 represented by the fibers at one end of each particle. In the recombinant pIII gene 34 of these phage, a mixture of oligonucleotides 35 encoding a library of conotoxin-like domains has been inserted. Each phage DNA has a conopeptide insert 35 with a different sequence. As a result, functional pIII protein is expressed and the phage is infective. However, on each phage particle, pIII protein is fused to a different conopeptide sequence which is exposed on the surface of the fUSE phage. These conopeptide modules 36, 37 and 38 are illustrated in FIG. 1C. at the distal tips of the pIII protein 33.

EXAMPLE 1
fUSE5/α-Conotoxin-like Library

FIG. 2 shows the actual sequences of some of the constructs proposed for use with a fUSE5 vector. FIG. 2A. shows the cloning site of the pIII structural gene, with the stuffer fragment (within the enclosed lines) present. The fUSE5 RF DNA is digested with the restriction enzyme SfiI to release the internal 14 bp stuffer fragment shown from the fUSE5 pIII coding sequence. The frameshift in the pIII gene is restored at this site by the insertion of oligonucleotides specifying α-conotoxin-like sequences, and having a length of (3n+1), where n equals the number of amino acid residues encoded, e.g. the inserted oligonucleotide.

FIG. 2B. illustrates the sequence of the actual oligonucleotide synthesized to construct an α-conotoxin MI insert into fUSE5, and the amino acid sequence of the expressed conotoxin module fused to the pIII protein.

FIG. 2C. illustrates a mixed oligonucleotide containing information specifying an α-conotoxin-like library, and the generalized conotoxin module that is expressed as an N-terminal fusion to the pIII protein. The 5'-phosphorylated oligonucleotide is shown having the sequences: 5' GG AGG TGC TGT CAT CCC GCG TGC NNK NNK NNK NNK NNK TGC GGC GGC ATT GAA GGT CGC GCT G [Seq.ID NO:13], where N represents a random distribution of all four bases (A, T, G and C) in equimolar amounts and K a random distribution of equal amounts of G and T bases.

This family of sequences can be mixed with a 5'-phosphorylated oligonucleotide of the patch sequence 5' ATGACAGCACCTCCCGT 3'[Seq.ID NO:14], and ligated to the SfiI-cut fUSE5 DNA vector as shown in FIG. 2A following removal of the 15 bp stuffer sequences. Filling-in of the resulting single strand plasmid DNA with DNA polymerase and electroporation into E. coli cell, followed by cell growth and phage production, results in the generation of an α-conotoxin-like library displayed on the bacteriophage surface. The primary translation product for each member of this library is a protein having the native N-terminal pIII signal sequence followed by the amino acids ala-asp, the α-conotoxin like domain, a linker sequence Gly-Gly-Ile-Glu-Gly-Arg-Ala-Gly-Ala [Seq.ID NO:1] which contains the Factor Xa cleavage site Ile-Glu-Gly-Arg [Seq.ID NO:2], and finally, the N-terminally truncated pIII protein. Following signal peptidase cleavage, which removes the N-terminal signal sequence, mature recombinant pIII coat proteins can be expressed on the surface of the bacteriophage each having an N-terminal ala-asp dipeptide sequence followed by the conopeptide module, and an α-conotoxin-like domain. In the α-conotoxin-like domain the amino acid sequences Xaa indicates that any of the 20 standard amino acids (including Cys) may be present at the indicated positions. Note the Formula I, 2-loop framework which, in general should result from the four Cys residues occurring at fixed positions in the amino acid sequences of the α-conotoxin-like peptides.

EXAMPLE 2
fUSE11/α-Conotoxin-like Library

New phage vectors have been designed which increase the flexibility of fUSE/conoeffector library construction. The cloning site sequence and general features of the fUSE11 vector are shown in FIG. 3. With reference to FIG. 3A., cleavage of fUSE11 RF DNA with restriction enzymes BsaI and BanII releases an internal 18 bp stuffer fragment (within the enclosed lines) and generates unique free ends for inserting single sequence (as well as multiple sequence) library constructions. The fUSE11 cloning strategy (also illustrated in FIG. 2) relies on the generation of two minus-strand single stranded overhangs which cannot be religated in the absence of bridging nucleotides, and obviates the need for a patch sequence in cloning the single stranded oligonucleotide encoding the conotoxin-like peptides.

In the most straightforward strategy, cloning is effected by ligating a single oligonucleotide strand to the restriction enzyme cut, stuffer fragment free, fUSE11 vector. As shown in both FIGS. 3B. and 3C., this oligonucleotide has a 5' end which contains the nucleotide sequence CAGC and is therefore complementary to the fUSE11 BstI overhang. The oligonucleotide also has at its 3' end the nucleotide sequence AGCC which is complementary to the fUSE11 BanII overhang. Ligation of the 5'-phosphorylated bridging strand oligonucleotide is followed by filling in of the single strand portion of the ligated structure with the addition of complementary nucleotides followed by electroporation into E. coli. With reference to FIG. 3B. an "α-conotoxin-like conopeptide library can be generated in the fUSE11 vector by using a 5'-phosphorylated bridging oligonucleotide which has the sequence C AGC GGG AGG TGC TGT NNK NNK NNK TGC NNK NNK NNK NNK NNK TGC GGC GGC ATT GAA GGT CGT GGA GCC [Seq.ID NO:3] where N is an equimolar mixture of bases G, A, T and C, and K is an equimolar mixture of G and T. The primary translation products of this construction following signal sequence cleavage and removal processing represent a library of α-conotoxin-like peptides fused to a truncated N-terminus of pIII. As illustrated in FIG. 3B., for each expressed, mature fusion peptide, the N-terminal domain begins with the authentic MI-α-conotoxin N-terminal sequence Gly-Arg-Cys-Cys [Seq.ID NO:4] which is followed by random amino acids "Xaa" in positions corresponding to the two inter-Cys domains of the MI α-conotoxin. Linking the conoeffector portion of the fusion library to pIII sequence is the bridging amino acid sequence Gly-Gly-Ile-Glu-Gly-Arg-Ala [Seq.ID NO:5] which contains the Factor Xa cleavage site Ile-Glu-Gly-Arg [Seq.ID NO:2] which allows clipping off the conotoxin-like module from the phage coat for detailed analysis.

FIG. 3C. is similar to FIG. 3B. but shows the oligonucleotide sequence for insertion into the fUSE11 vector for generating an ω-conotoxin-like library. This 5'-phosphorylated oligonucleotide has the sequence C AGC TGT $(NNK)_6$ TGC $(NNK)_6$ TGC TGT $(NNK)_3$ TGT $(NNK)_4$ TGT GGC GGC ATT GAA GGT CGT GGA GCC [Seq.ID NO:6] where N is an equimolar mixture of bases G, A, T and C and K is an equimolar mixture of G and T. The predicted amino acid sequence of the ω-conotoxin-like peptide is also shown in FIG. 3C.

Note in FIG. 3B. the Formula I, 2-loop framework arising from the four invarient Cys positions in the amino acid sequences of the α-conotoxin-like peptides and in FIG. 3C. the Formula III, 4-loop framework arising from the six invariant Cys positions of the ω-conotoxin-like peptides.

The invention is not limited to the use of fUSE5 or fUSE11 bacteriophage vectors nor to the pIII coat protein as the carrier fusion protein. Other fUSE and additional vectors can also be utilized for conopeptide library construction. The major phage coat protein, pVIII, which occurs in over a thousand copies on the phage, is also considered a target fusion protein for the display of the conopeptide modules. The appropriate choice of vector can change the design and type of the protease cleavage site and the C-terminal amino acids. Also, through proper design, the linker region between the conoeffector and pIII protein can be varied to enhance the steric availability of phage-borne conopeptide fusion product for binding to a receptor.

There are many, many variations possible in constructing conoeffector libraries. For example, using only the α-conotoxin like peptides, which have a 2-loop disulfide framework, the nucleotides encoding the second loop of five amino acids can be varied randomly to produce 3.2 million possible sequence variants which can be presented on the pIII protein. The $\mu$- and ω-conotoxins have 3- and 4-loop frameworks and libraries based on these disulfide frameworks present much greater variation.

It should be emphasized that although the examples given above are presently among the state-of-the-art vectors, technology development will continue unabated with regard to vector development. However, the general strategy will not change, although the details of the vector to be used undoubtedly will.

One direction in which vector development may go is in the development of different alternative linkers between the conopeptide modules and the pIII protein, in the conoeffector fusion construct. Optimum interaction between a conoeffector and a particular receptor target may require proper presentation of the conoeffector on the surface of the virion. This could depend both on the receptor target for which a "designer conopeptide" is being screened, as well as the disulfide structure of the conoeffector insert (e.g., 2-loop vs 4-loop, etc.). The efficacy of presentation in the conoeffector library can be assessed by evaluating binding of conoeffectors derived from peptides of known sequence and ligand specificity to their characterized receptors. Thus, the effects on binding of, for example, a fUSE11/ω-conotoxin phage which contains a natural ω-conotoxin sequence to a target $Ca^{++}$ channel can be used to evaluate the optimum linker construct for the "4-loop" conopeptide libraries (of which ω-conotoxin is an example). However, if in addition to the disulfide structure of the conopeptide module, optimum presentation is also strongly dependent in an idiosyncratic manner on the intended receptor target, conoeffector libraries with several different linker designs would be screened each time a new receptor target is used.

"Biopanning" or Screening of Conoeffector Libraries

Once a conoeffector library has been constructed, the members of the library with the desired targeting specificity need to be identified by screening. The receptor target protein of interest will be used to screen the library for unique, tight-binding conoeffectors. The general strategy is to present the target receptor in an immobilized form to the library or in solution, followed by immobilization. If the conoeffector library is a fUSE phage, as in the above examples, then the phage of interest will become immobilized with the target protein, and non-binding members of the library can be washed away. The bound phage are then eluted from the immobilized receptor amplified by infection of bacterial cells with each phage clone (by about $10^7$), followed by growth on solid bacterial medium. This procedure is referred to as "Biopanning" and plate amplification. Several cycles of Biopanning followed by plate amplification are carried out to enrich for those phage with the highest affinity to the immobilized target protein. A chief advantage of this library combined with these methods is to provide information for synthesizing conopeptides that bind specifically, and with high affinity to target proteins, especially receptors.

A principle advantage of the present invention is that one can first select the receptor target and then clonally select and expand the conopeptides which have affinity for that receptor. Then similarly structured peptides having the same disulfide bond framework can be screened against that receptor and those with optimum activity selected for further biological applications and structural study.

Each class of conotoxin peptides appears to be specifically targeted to a macromolecular receptor. The ω-conotoxins have high affinity for certain $Ca^{++}$ channel targets. The α-conotoxins are the major post-synaptic paralytic toxins targeted to acetylcholine receptors. At present, the nicotinic acetylcholine receptor from the electric ray, Torpedo, is the principal accessible α-conotoxin receptor target even though the intrinsic affinity of most α-conotoxin peptides is not as high as might be desired ($K_D$ approx $10^{-8}$M). In addition, corresponding conoeffector modules in a fusion phage will probably have lower affinity for the receptor than the free peptide. On the other hand, the ω-conotoxin phage present the converse picture, i.e. the affinity is very impressive for chick brain Ca channels, the suggested test receptor, ($K^D$ of approx $10^{-13}$M)—however, the receptor target is not as well characterized.

For the screening to function it is necessary that a sufficient fraction of the conopeptide have the biologically-active, disulfide-bonded configuration to bind to the receptor or other protein. However, providing the folding of the molecule, which may occur spontaneously during phage production, through use of a prepropeptide configuration or by chemical or enzymatic modification of the library, mimics or is the same as the active conotoxin framework, the conoeffector module will be satisfactory even if there are different magnitudes of affinity.

As referenced above, upon initial screening, the phage that bind with reasonable affinity can be enriched by multiple cycles of binding to the receptor followed by phage amplification. The phage bound to the receptor in the first round are washed, and eluted in acid in the manner described by Smith et al., supra, or dissociated from the receptor by some other means (such as incubation with a reducing agent or a free, competing ligand). The eluted phage are then amplified on agar medium, purified and subjected to additional rounds of affinity purification followed by plate amplification to yield only the highest affinity conoeffectors. As a percent of input phage, the yields from second, third or even higher rounds of biopanning and plate amplification are often, but not always, significantly above the background of nonspecific adsorption which indicates a high proportion of ligate-binding conoeffector clones.

The phage in the eluates of the second, third and successive rounds of biopanning can be cloned, tested for binding, and the DNA from each tight binding clone extracted. The DNA's can then be sequenced to determine the amino acid sequences encoding the conopeptide regions of the fusion proteins. The appropriate conopeptide analogs of those peptides displayed by tight binding phage can then be made by chemical synthesis. When using this method to design conopeptides, it can be done with the knowledge that, as the phage-borne peptides, the synthetic peptide should bind to the same target receptor as used for screening. Once a desired conoeffector with the desired specificity is obtained, its detailed conformation can be determined by 2D NMR or X-ray methods. The structure can in turn be a lead for designing non-peptidic organic compounds referred to as "peptidomimetics."

EXAMPLE 3

Biopanning with Nicotinic Acetylcholine Receptor

In this example the nicotinic acetylcholine receptor from Torpedo electric organ was used. The basic strategy is to immobilize the receptor by using streptavidin-coated 60 mm polystyrene plates. Because the acetylcholine receptor is glycosylated, the receptor can be linked to the streptavidin by using biotinylated lectins. Thus, the immobilized streptavidin binds the biotin moiety on the lectin, which in turn binds the glycosyl residues on the receptor, thereby tethering the receptor to the immobilized streptavidin.

The surface of each plate covered with 2 ml of 0.1M $NaHCO_3$, then 20 $\mu$l of 1 mg/ml streptavidin is added and the plate incubated overnight at 4° C. The liquid is removed and the plate is blocked by the addition of with 18 ml of 29 mg/ml bovine serum albumin (BSA), and incubated at room temperature for 1 hr. The BSA solution is removed and the plate is washed three times with modified Ringers solution containing 4% Triton X-100 and the plate is then shaken out.

The solubilized acetylcholine receptor (~1 $\mu$M receptor in MRT buffered, modified Ringers, 4% Triton X-100) is mixed with a mixture of two biotinylated lectins (concanavalin A and wheat germ agglutinin) and incubated at 4° C. for 30 minutes. The receptor/biotinylated lectin solution is then immediately added to the washed plate and incubated for 15 minutes at room temperature then the solution is removed and the plate washed with MRT buffer. At this step, the receptor is immobilized and ready for biopanning the phage library. A solution containing the phage library is then added to the plate and incubated overnight at 4° C. The unbound phage are removed by several round of washing in MRT buffer, and the bound phage eluted with acid. The enriched phage are amplified by infecting *E. coli* cells and grown on plates containing agar medium. Amplified phage are purified after growth and used in a further round of biopanning.

The enriched phage obtained after successive rounds of biopanning and plate amplification are then cloned. Each clone is tested for binding to receptor and the DNA from each clone extracted and sequenced to determine the encoded amino acid sequences using conventional sequencing techniques.

While certain representative embodiments of the invention have been described herein for purposes of illustration, the invention may be embodied in other specific forms without departing from its spirit or essential characteristics, and the described examples should not be considered restrictive, but only illustrative. The scope of the invention is therefore defined by the appended claims rather than by the foregoing examples.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 9 amino acids
( B ) TYPE: amino acids residues
( D ) TOPOLOGY: linear ( x i ) SEQUENCE DESCRIPTION: SEQ ID NO:1:

Gly Gly Ile Glu Gly Arg Ala Gly Ala
1 5

( 2 ) INFORMATION FOR SEQ ID NO:2:

( i ) SEQUENCE CHARACTERISTICS:
    ( A ) LENGTH: 4 amino acid residues
    ( B ) TYPE: amino acids
    ( D ) TOPOLOGY: linear ( x i ) SEQUENCE DESCRIPTION: SEQ ID NO:2:

Ile Glu Gly Arg ( 2 ) INFORMATION FOR SEQ ID NO:3:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CAGCGGGAGG  TGCTGTNNKN  NKNNKTGCNN  KNNKNNKNNK  NNKTGCGGCG  GCATTGAAGG        60

TCGTGGAGCC                                                                    70
```

( 2 ) INFORMATION FOR SEQ ID NO:4:

( i ) SEQUENCE CHARACTERISTICS:
        ( A ) LENGTH: 4 amino acid residues
        ( B ) TYPE: amino acids
        ( D ) TOPOLOGY: linear ( x i ) SEQUENCE DESCRIPTION: SEQ ID NO:4:

Gly Arg Cys Cys ( 2 ) INFORMATION FOR SEQ ID NO:5:

( i ) SEQUENCE CHARACTERISTICS:
        ( A ) LENGTH: 7 amino acid residues
        ( B ) TYPE: amino acid
        ( D ) TOPOLOGY: linear ( x i ) SEQUENCE DESCRIPTION: SEQ ID NO:5:

Gly Gly Ile Glu Gly Arg Ala
 1             5

( 2 ) INFORMATION FOR SEQ ID NO:6:

( i ) SEQUENCE CHARACTERISTICS:
        ( A ) LENGTH: 103 base pair
        ( B ) TYPE: nucleic acid
        ( C ) STRANDEDNESS: single
        ( C ) TOPOLOGY: linear ( x i ) SEQUENCE DESCRIPTION: SEQ ID NO:6:

```
CAGCTGTNNK  NNKNNKNNKN  NKNNKTGCNN  KNNKNNKNNK  NNKNNKTGCT  GTNNKNNKNN        60

KTGTNNKNNK  NNKNNKTGTG  GCGGCATTGA  AGGTCGTGGA  GCC                          103
```

( 2 ) INFORMATION FOR SEQ ID NO:7:

( i ) SEQUENCE CHARACTERISTICS:
        ( A ) LENGTH: 70 base pairs
        ( B ) TYPE: nucleic acid
        ( C ) STRANDEDNESS: single
        ( C ) TOPOLOGY: linear ( x i ) SEQUENCE DESCRIPTION: SEQ ID NO:7:

```
TCGGCCGACG  TGGCCTGGCC  TCTGGGGCCG  AAACTAGCCG  GCTGCACCGG  ACCGGAGACC        60

CCGGCTTTGA                                                                    70
```

( 2 ) INFORMATION FOR SEQ ID NO:8:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

```
TCG  GCC  GAC  GGG  AGG  TGC  TGT  CAT  CCC  GCG  TGC  GGT  AAA  AAC              42
Ala  Asp  Gly  Arg  Cys  Cys  His  Pro  Ala  Cys  Gly  Lys  Asn
 1                    5                        10

TAT  TCG  TGC  GGC  GGC  ATT  GAA  GGT  CGC  GCT  GGG  GCCGAAACTA                  85
Tyr  Ser  Cys  Gly  Gly  Ile  Glu  Gly  Arg  Ala  Gly
      15                    20

GCCGGCTGCC  CTCCACGACA  GTAGGGCGCA  CGGACCCCGG  CTTTGA                            131
```

( 2 ) INFORMATION FOR SEQ ID NO:9:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

```
TCG  GCC  GAC  GGG  AGG  TGC  TGT  CAT  CCC  GCG  TGC  NNK  NNK  NNK  NNK         45
Ala  Asp  Gly  Arg  Cys  Cys  His  Pro  Ala  Cys  Xaa  Xaa  Xaa  Xaa
 1                    5                        10

NNK  TGC  GGC  GGC  ATT  GAA  GGT  CGC  GCT  GGG  GCCGAAACTA                       85
Xaa  Cys  Gly  Gly  Ile  Glu  Gly  Arg  Ala  Gly
 15                        20

GCCGGCTGCC  CTCCACGACA  GTAGGGCGCA  CGGACCCCGG  CTTTGA                            131
```

( 2 ) INFORMATION FOR SEQ ID NO:10:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

```
ATTCTCACAG  CGGAGACCTG  GAGCCCCTGG  CGCTGAAACT  TAAGAGTGTC  GCCTCTGGAC             60
CTCGGGGACC  GCGACTTTGA                                                             80
```

( 2 ) INFORMATION FOR SEQ ID NO:11:

( i ) SEQUENCE CHARACTERISTICS:
    ( A ) LENGTH: 123 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

```
ATTCTCACAG  C  GGG  AGG  TGC  TGT  NNK  NNK  NNK  TGC  NNK  NNK  NNK              44
               Gly  Arg  Cys  Cys  Xaa  Xaa  Xaa  Cys  Xaa  Xaa  Xaa
                1                    5                        10

NNK  NNK  TGC  GGC  GGC  ATT  GAA  GGT  CGT  GGA  GCC  CCTGGCGCTG                  87
Xaa  Xaa  Cys  Gly  Gly  Ile  Glu  Gly  Arg  Gly  Ala
           15                        20

GAAACTTAAG  AGTGTCGTCG  GGACCGCGA  CTTTGA                                         123
```

( 2 ) INFORMATION FOR SEQ ID NO:12:

( i ) SEQUENCE CHARACTERISTICS:
  ( A ) LENGTH: 155 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:12:

```
ATTCCCACAG C TGT NNK NNK NNK NNK NNK NNK TGC NNK NNK NNK          44
            Cys Xaa Xaa Xaa Xaa Xaa Xaa Cys Xaa Xaa Xaa
             1                   5                  10

NNK NNK NNK TGC TGT NNK NNK NNK TGT NNK NNK NNK NNK TGT GGC       89
Xaa Xaa Xaa Cys Cys Xaa Xaa Xaa Cys Xaa Xaa Xaa Xaa Cys Gly
         15                  20                  25

GGC ATT GAA GGT CGT GGA GCC CCTGGCGCTG AAACTTAAGA                130
Gly Ile Glu Gly Arg Gly Ala
         30

GTGTCGTCGG GGACCGCGAC TTTGA                                     155
```

( 2 ) INFORMATION FOR SEQ ID NO:13:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

```
GGAGGTGCTG TCATCCCGCG TGCNNKNNKN NKNNKNNKTG CGGCGGCATT GAAGTTCGCG   60

CTG                                                                63
```

( 2 ) INFORMATION FOR SEQ ID NO:14:

( i ) SEQUENCE CHARACTERISTICS:
    ( A ) LENGTH: 17 base pair
    ( B ) TYPE: nucleic acid
    ( C ) STRANDEDNESS: single
    ( D ) TOPOLOGY: linear ( x i ) SEQUENCE DESCRIPTION: SEQ ID NO:14:

```
ATGACAGCAC CTCCCGT                                                 17
```

( 2 ) INFORMATION FOR SEQ ID NO:15:

( i ) SEQUENCE CHARACTERISTICS:
    ( A ) LENGTH: 8 amino acid residues
    ( B ) TYPE: amino acid
    ( D ) TOPOLOGY: linear ( x i ) SEQUENCE DESCRIPTION: SEQ ID NO:15:

```
Cys Cys Xaa Xaa Cys Xaa Xaa Cys
 1               5
```

( 2 ) INFORMATION FOR SEQ ID NO:16:

( i ) SEQUENCE CHARACTERISTICS:
    ( A ) LENGTH: 12 amino acid residue
    ( B ) TYPE: amino acid
    ( D ) TOPOLOGY: linear ( x i ) SEQUENCE DESCRIPTION: SEQ ID NO:16:

```
Cys Cys Xaa Xaa Cys Xaa Xaa Cys Xaa Xaa Cys Cys
 1               5                  10
```

( 2 ) INFORMATION FOR SEQ ID NO:17:

(i) SEQUENCE CHARACTERISTICS:
  (A) LENGTH: 14 amino acid residue
  (B) TYPE: amino acid
  (D) TOPOLOGY: linear (xi) SEQUENCE DESCRIPTION: SEQ ID NO:17:

Cys Xaa Xaa Cys Xaa Xaa Cys Cys Xaa Xaa Cys Xaa Xaa Cys
 1               5                           10

(2) INFORMATION FOR SEQ ID NO:18:

(i) SEQUENCE CHARACTERISTICS:
    (A) LENGTH: 14 amino acid residue
    (B) TYPE: amino acid
    (D) TOPOLOGY: linear (xi) SEQUENCE DESCRIPTION: SEQ ID NO:18:

Cys Xaa Xaa Cys Xaa Xaa Cys Xaa Xaa Cys Cys Xaa Xaa Cys
 1               5                           10

(2) INFORMATION FOR SEQ ID NO:19:

(i) SEQUENCE CHARACTERISTICS:
    (A) LENGTH: 14 amino acid residue
    (B) TYPE: amino acid
    (D) TOPOLOGY: linear (xi) SEQUENCE DESCRIPTION: SEQ ID NO:19:

Cys Xaa Xaa Cys Xaa Xaa Cys Xaa Xaa Cys Xaa Xaa Cys Cys
 1               5                           10

(2) INFORMATION FOR SEQ ID NO:20:

(i) SEQUENCE CHARACTERISTICS:
    (A) LENGTH: 24 amino acid residues
    (B) TYPE: amino acid
    (C) STRANDEDNESS: single
    (D) TOPOLOGY: linear (xi) SEQUENCE DESCRIPTION: SEQ ID NO:20:

Ala Asp Gly Arg Cys Cys His Pro Ala Cys Gly Lys Asn
 1               5                           10

Tyr Ser Cys Gly Gly Ile Glu Gly Arg Ala Gly
     15                      20

(2) INFORMATION FOR SEQ ID NO:21:

(i) SEQUENCE CHARACTERISTICS:
    (A) LENGTH: 24 amino acid residues
    (B) TYPE: amino acid
    (C) STRANDEDNESS: single
    (D) TOPOLOGY: linear (xi) SEQUENCE DESCRIPTION: SEQ ID NO:21:

Ala Asp Gly Arg Cys Cys His Pro Ala Cys Xaa Xaa Xaa Xaa
 1               5                           10

Xaa Cys Gly Gly Ile Glu Gly Arg Ala Gly
     15                      20

(2) INFORMATION FOR SEQ ID NO:22:

(i) SEQUENCE CHARACTERISTICS:
    (A) LENGTH: 22 amino acid residues
    (B) TYPE: amino acid
    (C) STRANDEDNESS: single
    (D) TOPOLOGY: linear (xi) SEQUENCE DESCRIPTION: SEQ ID NO:22:

```
Gly  Arg  Cys  Cys  Xaa  Xaa  Xaa  Cys  Xaa  Xaa  Xaa
 1              5                        10

Xaa  Xaa  Cys  Gly  Gly  Ile  Glu  Gly  Arg  Gly  Ala
               15                       20
```

(2) INFORMATION FOR SEQ ID NO:23:

(i) SEQUENCE CHARACTERISTICS:
      (A) LENGTH: 33 amino acid residues
      (B) TYPE: amino acid
      (C) STRANDEDNESS: single
      (D) TOPOLOGY: linear (xi) SEQUENCE DESCRIPTION: SEQ ID NO:23:

```
Cys  Xaa  Xaa  Xaa  Xaa  Xaa  Xaa  Cys  Xaa  Xaa  Xaa
 1              5                        10

Xaa  Xaa  Xaa  Cys  Cys  Xaa  Xaa  Xaa  Cys  Xaa  Xaa  Xaa  Xaa  Cys  Gly
               15                       20                       25

Gly  Ile  Glu  Gly  Arg  Gly  Ala
               30
```

We claim:

1. A method for the synthesis, identification and isolation of cloned, small, rigid, conotoxin-like peptides having Cys residues arranged to allow formation of multiple disulfide bonds characteristic of naturally occurring conotoxins but with remaining amino acids being variable in sequence and having binding specificities for target proteins which comprises:

(a) constructing a conotoxin-like peptide library consisting of conotoxin-like peptide modules by
      (i) preparing oligonucleotides, each of which has a nucleotide sequence encoding a potential conotoxin-like peptide wherein Cys residues are encoded at positions characteristic of natural conotoxins and random amino acid sequences are encoded at the other positions of the peptide region,
      (ii) inserting said oligonucleotides into an appropriate vector to yield a recombinant DNA vector for transfecting a host cell,
      (iii) transfecting a host cell to allow amplification of said recombinant vector in an infectious form thereby forming said conotoxin-like peptide library each member of which expresses a conotoxin-like peptide module;
   (b) reacting said conotoxin-like peptide library with a target protein which selectively binds vector bearing certain conotoxin-like peptide modules having an affinity for said target protein and removing unbound vector bearing non-binding conotoxin-like peptide modules from said target protein;
   (c) eluting said bound vector bearing conotoxin-like modules from said target protein and reinfecting said host cell with said vector to allow amplification of the recombinant DNA of said vector in an infectious form thereby producing amplified, enriched vector bearing conotoxin-like peptide modules having an affinity for said target protein;
   (d) reacting said amplified, enriched vector bearing conotoxin-like peptide modules with said target protein to selectively bind those vector bearing conotoxin-like modules having an affinity for said target protein and removing unbound vector bearing conotoxin-like peptide modules from said target protein;
   (e) repeating steps (c) and (d) in sequence to obtain vector bearing conotoxin-like peptide modules having high affinity for said target protein;
   (f) cloning individual vector bearing conotoxin-like peptide modules having high affinity for said target protein, and extracting their DNA therefrom; and
   (g) sequencing said DNA to determine the amino acid sequence of the conotoxin-like peptides from said modules.

2. A method according to claim 1 wherein said recombinant DNA for transfecting a host cell is prepared by inserting said oligonucleotides encoding a conotoxin-like peptide into a fusion phage vector.

3. A method according to claim 2 wherein said vector is a fUSE vector.

4. A method according to claim 3 wherein said infectious form in which said recombinant vector is amplified is a bacteriophage and wherein said conotoxin-like peptide modules are displayed on a protein coat surface of said phage.

5. A method according to claim 4 wherein said protein coat surface is a pIII protein.

6. A method according to claim 5 wherein said host cell is a bacterium.

7. A method according to claim 5 wherein the oligonucleotides are coded such that the specified codons for Cys are in fixed positions characteristic of a natural conotoxin peptide sequence having disulfide bonds defining a 2-loop structure framework.

8. A method according to claim 7 wherein said target protein is an acetylcholine receptor.

9. A method according to claim 7 further comprising chemically synthesizing a conotoxin-like peptide having the peptide sequence determined from said DNA sequencing.

10. A method according to claim 5 wherein the oligonucleotides are coded such that the specified codons for Cys are in fixed positions characteristic of a natural conotoxin peptide sequence having disulfide bonds defining a 4-loop structure framework.

11. A method according to claim 10 wherein said target protein is a calcium channel receptor.

12. A method according to claim 10 further comprising chemically synthesizing a conotoxin-like peptide having the peptide sequence determined from said DNA sequencing.

13. A method according to claim 5 wherein the oligonucleotides are coded such that the specified codons for Cys are in fixed positions characteristic of a natural conotoxin peptide sequence having disulfide bonds defining a 3-loop structure framework.

14. A method according to claim 13 wherein said target protein is a sodium channel receptor.

15. A method according to claim 13 further comprising chemically synthesizing a conotoxin-like peptide having the peptide sequence determined from said DNA sequencing.

16. A method according to claim 5 wherein the oligonucleotide sequence is coded such that the specified codons for Cys are in fixed positions which are characteristic of conotoxins but are not strictly conotoxin structure specific.

17. A method according to claim 16 further comprising chemically synthesizing a conotoxin-like peptide having the peptide sequence determined from said DNA sequencing.

18. A method according to claim 4 wherein said target protein is a receptor.

19. A method according to claim 6 wherein said bacterium is *E. coli*.

20. A method according to claim 5 wherein the vector is a fUSE5 vector.

21. A method according to claim 5 wherein the vector is a fUSE11 vector.

* * * * *